(12) United States Patent
Hilgers et al.

(10) Patent No.: US 7,104,978 B2
(45) Date of Patent: Sep. 12, 2006

(54) DISPOSABLE ELEMENT FOR A DEVICE FOR CARRYING OUT A MEDICAL TREATMENT USING A LIQUID

(75) Inventors: Peter Hilgers, Schonungen (DE); Matthias Brandl, Bad Koenigshofen (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 445 days.

(21) Appl. No.: 10/149,540

(22) PCT Filed: Dec. 8, 2000

(86) PCT No.: PCT/EP00/12417

§ 371 (c)(1),
(2), (4) Date: Nov. 5, 2002

(87) PCT Pub. No.: WO01/41834

PCT Pub. Date: Jun. 14, 2001

(65) Prior Publication Data

US 2003/0135193 A1    Jul. 17, 2003

(30) Foreign Application Priority Data

Dec. 8, 1999    (DE) ................................. 199 59 230

(51) Int. Cl.
A61B 19/00    (2006.01)
B65D 30/20    (2006.01)

(52) U.S. Cl. ................... 604/408; 604/403; 383/120

(58) Field of Classification Search ................ 604/403, 604/408, 410, 905; 220/62.22; 206/363–366, 206/438, 828; 383/210.1, 41, 67, 105, 42, 383/120; 128/DIG. 24

See application file for complete search history.

(56) References Cited

U.S. PATENT DOCUMENTS

| 4,397,643 | A | * | 8/1983 | Rygiel | 604/317 |
| 4,573,992 | A | * | 3/1986 | Marx | 604/408 |
| 4,617,115 | A | * | 10/1986 | Vantard | 210/90 |
| 5,364,385 | A | | 11/1994 | Harms et al. | |
| 5,607,082 | A | | 3/1997 | Cracauer | |
| 5,858,015 | A | * | 1/1999 | Fini | 604/403 |
| 6,682,517 | B1 | * | 1/2004 | Ezaki et al. | 604/410 |

FOREIGN PATENT DOCUMENTS

| DE | 31 15 665 | 11/1982 |
| DE | 94 17 416 | 2/1995 |
| DE | 198 25 158 | 4/1999 |
| FR | 2 749 763 | 12/1997 |

* cited by examiner

Primary Examiner—Patricia Bianco
Assistant Examiner—Leslie R. Deak
(74) Attorney, Agent, or Firm—Kenyon & Kenyon LLP

(57) ABSTRACT

The invention relates to a disposable element for a medical treatment device, especially a hemodialysis device. The inventive disposable element comprises a film bag filled with the dialysis liquid that consists of two superimposed flat films or a tubular film with connections for supplying and discharging the liquid. The film bag or the tubular film, in the condition ready for usage, is closed with a first weld on the top end and with a second weld on the lower end and is folded several times parallel to the longitudinal axis that is vertical in the condition ready for usage. The film bag is inserted in a receiving unit that is configured as a shaping dish that has a middle cylindrical section followed by an upper or lower convex section. The inventive disposable element, when combined with the receiving unit, unfolds more easily when being filled and has a lesser tendency to form creases.

40 Claims, 7 Drawing Sheets

DISPOSABLE ELEMENT FOR A DEVICE FOR CARRYING OUT A MEDICAL TREATMENT USING A LIQUID

FIELD OF THE INVENTION

The present invention relates to a disposable for a device for carrying out a medical treatment using a fluid. Moreover, the invention relates to a device for carrying out a medical treatment using a fluid, and also indicates the use of the disposable in a hemodialysis device.

BACKGROUND OF THE INVENTION

Hemodialysis devices are known in various designs. The material exchange between the blood and the dialyzing fluid takes place in a dialyzer which has a first flow path for the blood and a second flow path for the dialyzing fluid, both flow paths being separated from each other by a semipermeable membrane. The first flow path is a component of an extracorporeal blood circulation having a feed line and a return line for the blood, as well as, if desired, a pump supporting the blood flow. The second flow path is connected to devices for feeding and removing the dialyzing fluid. In addition to the so-called single-pass systems, in which the continually supplied dialyzing fluid passes the dialyzer only once and is then discarded, so-called batch systems are also known. The German Patent 31 15 665 C2 describes such a hemodialysis device which works with a volumetrically-fixed container, sealed off against the atmosphere, which is completely filled with fresh dialyzing fluid prior to beginning the treatment. During operation, fluid is pumped out of the container through the dialyzer, and the used fluid is fed back into the container again. Because of the constant volume of the entire system filled with the dialyzing fluid, ultra-filtration can only be carried out when fluid is removed from the system. A mixture of fresh and used dialyzing fluid is avoided in the known hemodialysis device, in that the removal of the dialyzing fluid is carried out in the upper region of the container, while the feedback takes place in the lower container region. The stratification of the fresh dialyzing fluid with the used dialyzing fluid remains stable due to the maintenance of a vertical temperature gradient in the container from top to bottom.

The container is made of glass which is substantially resistant to chemicals to be considered, cleans well and is physiologically unobjectionable. However, it is disadvantageous that the glass container is comparatively costly to produce and relatively difficult to clean.

The German Patent 198 25 158 C1 describes a disposable, constructed as a film bag, which, together with a shaping vessel, is able to replace the glass container, relatively expensive to produce, of the hemodialysis device which is described in DE 31 15 665 C2 mentioned at the outset. The disposable is made of two twisted-conical sections which are welded together at their peripheral edge to form a double cone. The special advantage of this form design is that the disposable can be produced from conventional (flat) films. A three-dimensional fashioning as, for example, in the case of disposable gloves, is not necessary for this.

The glass container can only be replaced by the film bag if the volumetric constancy, sterility and fluid stratification are guaranteed.

To ensure the volumetric constancy, the bag must be able to unfold reproducibly and completely in the pressure-stable vessel with defined volume while being filled. Air pockets between bag and vessel, which develop due to unfoldings or spaces to be bridged, must be largely avoided. Creases caused by the geometry can only be accepted if they are reproducible, and the volume enclosed by them is negligible compared to the total volume. To ensure sterility, the interior of the bag must not be opened during the dialysis preparation, and during the filling, should only come in contact with the fluid flowing in. For the fluid stratification, the shape of the bag must support a clear separation between fresh and used dialyzing fluid. In addition, the bag should be easy to handle and inexpensive to produce.

French Patent publication no. FR 2 749 763 describes a method for producing a salt concentrate for the hemodialysis. The salt concentrate is made available in a bag which is folded from a tubular film. It is a side-fold bag which is able to unfold to form a rectangular packet.

The U.S. Pat. No. 5,607,082 describes a tank for a compression sprayer having an outer container which accommodates an inner container. The inner container has a rigid back wall and is folded like a concertina.

From DE 9417416 U1, a secretion-collecting bag is known which is able to fold together like a concertina.

SUMMARY OF THE INVENTION

The object of the present invention is to provide a disposable for a medical treatment device, the disposable being easy to handle, inexpensive to produce and ensuring the necessary volumetric constancy, sterility and fluid stratification, and to indicate a medical treatment device for the disposable, as well as the use of the disposable in a hemodialysis device.

This objective is achieved by the subject matter of claims 1 and 12, respectively, and by the use according to claim 11.

The disposable according to the present invention is produced from two superposed flat films or one tubular film, it being possible to dispense with the one or two longitudinal welded seams for sealing the superposed flat films when using a tubular film.

At the upper end in the position of normal use, the film bag or the tubular film is sealed by a first welded seam, and at the lower end by a second welded seam. Both welded seams preferably have an outwardly curved profile. The unfolded film bag therefore preferably has a cylindrical segment which is adjoined by an outwardly curved upper segment and an outwardly curved lower segment. The same holds true for the tubular film.

However, to be understood by outwardly curved welded seams are also welded seams composed of a plurality of straight sections. Thus, instead of arched welded seams, it has proven to be advantageous in practice to provide welded seams having straight sections which approximate the profile of the curved welded seams. Such welded seams are particularly simple to make from the standpoint of production engineering.

The medical treatment device has a receiving unit, configured as a shaping dish, for the disposable. The shaping dish has a middle cylindrical contact surface, adjoined by an outwardly curved upper contact surface and an outwardly curved lower contact surface. Thus, the dish has the distinction of a high pressure-stability.

For the medical treatment, the disposable is inserted into the shaping dish. Since the flat surfaces are unable to uncoil precisely due to the curved terminations of the cylinder, the formation of creases in the film bag or the tubular film in the terminations is indeed unavoidable; however, in practice, it has turned out that the volume enclosed by the creases in the terminations is relatively slight compared to the total volume.

The film bag or the tubular film is folded repeatedly parallel to the longitudinal axis that is vertical in the position of normal use. The film bag or the tubular film is folded repeatedly in sections of equal size like a concertina, it being advantageous for a symmetrical design to select an uneven number of fold sections. To introduce the disposable, the shaping dish is provided with a cut-out in the upper contact surface. Since the folded film bag or the tubular film forms a flat strip, the dimensions of the cut-out may be small. Consequently, the forces acting on the cut-out by the system pressure are also small, so that the dish is very pressure-stable and the closure of the cut-out is simplified. Since complicated mechanisms, e.g. for swivelling the dish or the like, are not necessary, it is also relatively simple to manufacture the dish.

Because of the simple geometric shape, the disposable represents an arrangement which is inexpensive to produce and simple to handle. The bag shape favors the reproducible unfolding. Besides optimizing the expansion properties, the folding also has the advantage that the bag takes up less space during storage and transport.

To be able to provide the disposable as a flat strip, the folds are expediently fixed in position by joining elements, e.g. rivets, clips or the like, which are preferably disposed at the film ends. However, welded seams may also be provided transversely to the longitudinal axis.

In a preferred embodiment of the disposable of the present invention, at the first welded seam, a connecting part is welded to the bag film, the connecting part having at least one connection for supplying fluid and one connection for carrying fluid away. Attached to the connection for supplying fluid is a tube line, extending into the interior of the bag up to the second welded seam. Achieved by this is that fluid, e.g. used dialyzing fluid, may be fed to the lower half, and fluid, e.g. fresh dialyzing fluid, may be withdrawn from the upper half of the disposable.

In order to fix the tube line in position in the disposable, a fixation member to which the tube line is secured may be provided at the second welded seam.

The film bag or the tubular film is preferably made of a polyethylene base material which is provided on one side with a polyamide sealing layer.

In another preferred embodiment of the medical treatment device of the present invention, the lower end of the disposable may be fixed in position in the shaping dish. To that end, in the center of the lower contact surface, the dish is provided with a second cut-out into which a fixation device may be inserted with an exact fit for releasably securing the lower end of the disposable. The cut-out preferably has a cross-section which tapers downward, allowing a particularly simple positioning of the correspondingly shaped fixation device.

The fixation device is preferably able to be arrested in the dish. For example, a magneto coupling or even a clasp or the like may be provided for the fixation. It is only crucial that the catch be easily releasable by hand for exchanging the disposable.

To secure the upper end of the disposable, a further fixation device is preferably provided which is insertable with an exact fit into the cut-out for introducing the disposable into the dish. Thus, this fixation device is used, as it were, to seal the dish.

The second fixation device is preferably secured to a retaining device in a manner that it can be displaced longitudinally. During the filling of the disposable, the distance between its upper and lower ends decreases, the longitudinally displaceable fixation device closing the dish. Since the fixation device is arranged outside of the dish, the upper end of the disposable may easily be secured.

The folds define an orientation directed parallel to and an orientation directed perpendicular to the surface normals of the fold sections. These orientations are reinforced by the multilayer nature of the fold sections, which means they are retained fixed in space upon insertion of the disposable into the dish. The first and second fixation devices ensure that the bag is held taut during the filling. This guarantees that the filling process takes place under clearly defined conditions and is exactly reproducible.

The profile of the first and second welded seams is preferably selected so that the formation of creases in the cylinder terminations is minimized and reproducible. This may be achieved in particular by a curved welded seam which only produces creases transversely to the seam. When the disposable is filled, the tensions occurring are relatively slight in the case of a curved welded seam.

Experiments have shown that the disposable is able to unfold easily and flatten against the contact surfaces of the dish in particular if the distance between the ends of the first and second welded seams on one of the two longitudinal sides of the flat-lying film bag or of the tubular film is greater than the length of the cylindrical contact surface of the shaping dish. The distance should preferably be greater by an amount that is at least twice as large, preferably three times as large as the width of the folds of the film bag or of the tubular film.

A further improvement is achieved if, at the same time, the distance between the summit of the first and second welded seams, respectively, and the center point of the straight lines running through their ends, given a flat-lying film bag or tubular film, is less than the depth of the curved contact surface of the shaping dish. The curvature of the curved welded seams thereby becomes less, which means they may also be replaced by straight welded seams in their edge areas.

The disposable is preferably used in a hemodialysis device. However, it may also be used similarly as described in DE 198 25 158 C1 in a peritoneal dialysis device for making peritoneal dialysis solution available.

In the following, individual exemplary embodiments of the invention are explained in greater detail with reference to the drawings, in which:

DETAILED DESCRIPTION

Figure 1:
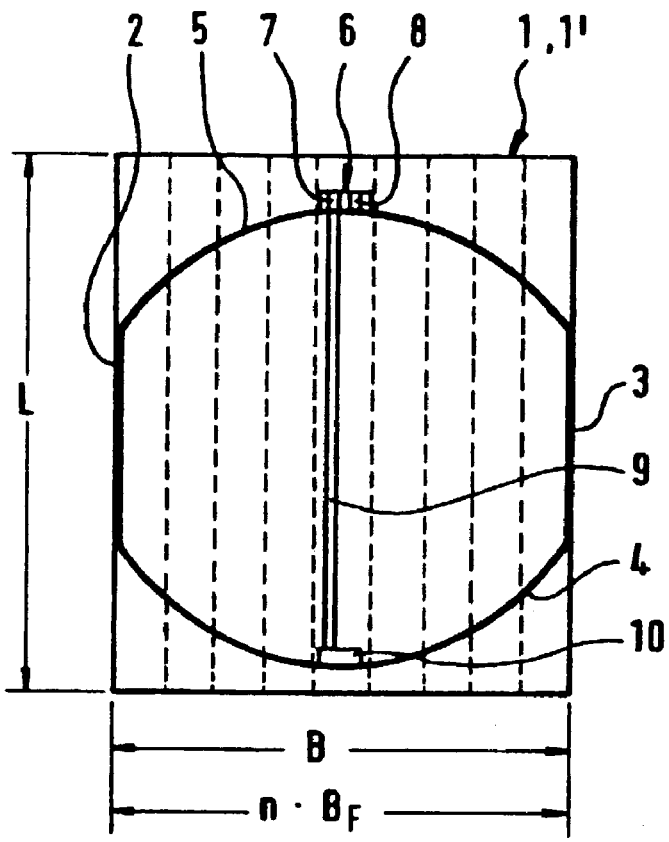
FIG. 1 shows a simplified representation of the flat-lying disposable in a plan view.

FIG. 1 shows the plan view of the flat-lying disposable in simplified representation. The disposable has two rectangular films 1, 1' having the length L and the width B, which lie congruently one upon the other and are sealed at the longitudinal sides by longitudinal welded seams 2, 3 and at the ends by outwardly curved welded seams 4, 5. A flat film is used as film material which is made of polyethylene (PE) as base material that is provided with a polyamide (PA) sealing layer on one side. The thickness of the film is 100 μm.

Instead of the superposed flat films, a film tube may also be used which is sealed at its ends by the curved welded seams. However, it is also possible to use one flat film which is folded on one side, is sealed only at one longitudinal side by a longitudinal welded seam and is closed at its ends by the curved welded seams.

The disposable is provided with a connecting part 6, shown only indirectly in FIG. 1, which, for example, is constructed as a type of shuttle and is sealed to the flat films. Connecting part 6 has one connection 7 for feeding fluid and one connection 8 for carrying fluid away. The tube lines of the medical treatment device are attached to connections 7 and 8.

Connecting part 6 is disposed at the summit of upper curved welded seam 5 in the position of normal use of the disposable. Attached to connection 7 for supplying fluid is a tube line 9 which extends into the interior of the bag up to lower curved welded seam 4 and whose free end is secured to a fixation piece 10 that is sealed at the summit of lower welded seam 4 to flat films 1, 1'. The flat-lying film bag is folded repeatedly parallel to its longitudinal axis like a concertina in sections of equal size. Width $B_F$ of the fold sections is calculated from the quotient of width B of the flat films and the number n of fold sections. For a symmetrical construction, it is expedient to select an uneven number of fold sections (e.g., n=9).

Figure 2:
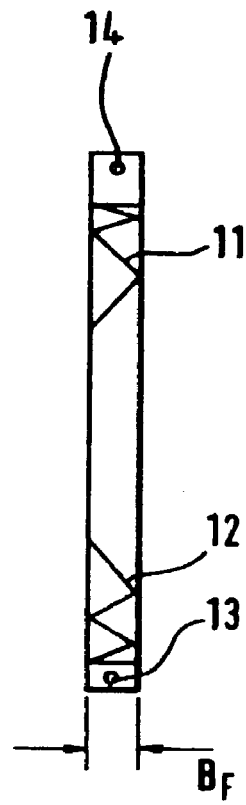
FIG. 2 shows the folded disposable from FIG. 1.
Figure 3:
FIG. 3 shows the concertina-like folding of the disposable.

FIG. 2 shows a plan view of the film bag of FIG. 1, folded like a concertina. The folded curved welded seams at the ends of the film bag are provided with reference numerals 11, 12. FIG. 3 shows the concertina-like folding of the film bag.

To fix the folds in position, joining elements 13, 14 are provided, shown only indirectly in FIG. 2, which are arranged at the ends of the film bag projecting beyond curved welded seams 4, 5. The joining elements are rivets by which the film stack is securely held together as a flat strip.

In the following description of an exemplary embodiment of the present invention, the receiving unit for the disposable is described with reference to FIGS. 4 through 7, the receiving unit being a component of the medical treatment device, e.g. of a hemodialysis device.

The receiving unit is constructed as a shaping dish in which the disposable, after unfolding, receives an exactly reproducible form. Shaping dish 15 has a middle cylindrical contact surface 16 which is adjoined by an outwardly curved upper contact surface 17 as top and an outwardly curved lower contact surface 18 as bottom. In this respect, the shaping dish forms a rotationally symmetrical hollow body which completely accommodates the disposable. Upper and lower contact surfaces 17, 18 have a curved contour in intersection. The distances between the summits of the arched contours of upper and lower contact surfaces 17, 18, respectively, and cylindrical contact surface 16, i.e. the height or depth of the outwardly curved sections, are designated in FIG. 4 by $S_1$ and $S_2$. Cylindrical section 16 has the length l.

Contact surfaces 17 and 18 may have an identical or different curvature, this likewise being valid for the geometric form of the disposable. Thus, it may be expedient to dispose upper curved surface 17 deeper so that as clearly a defined point as possible exists for the removal of dialyzing fluid. Furthermore, it may be advantageous if lower curved surface 18 has a flat curvature to minimize the overall height.

The dish is preferably made of a heat-insulating material or is provided with a thermal insulation.

Figure 5:
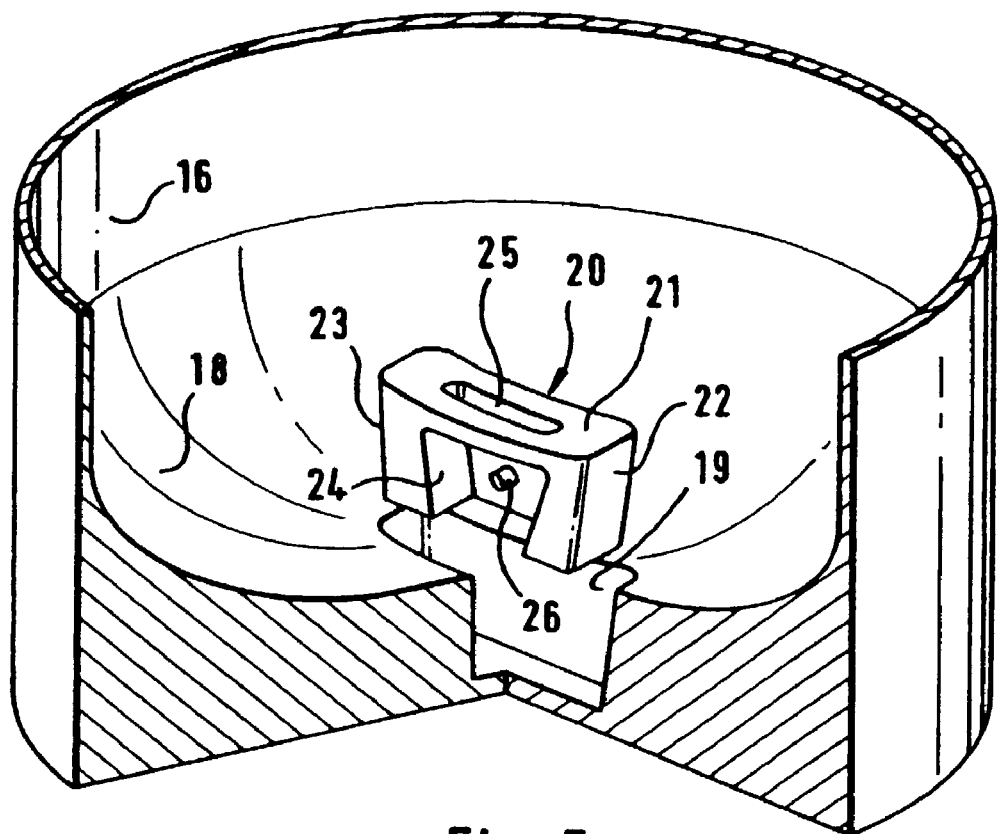
FIG. 5 shows the cut-away portion A of FIG. 4 in enlarged perspective representation.

In the center of the lower contact surface, dish 15 has a cut-out 19 into which a fixation device 20 is insertable with exact fit for securing the lower end of disposable D. Fixation device 20 is an oblong shaped part having an upper side 21 corresponding to the contour of lower contact surface 18, and two inwardly running narrow sides 22, 23, so that upon insertion into the dish, the shaped part is centered (FIG. 5).

One of the longitudinal sides of the shaped part is provided with a middle cut-out 24. At its upper side, the shaped part has an elongated hole 25 through which the lower end of folded disposable D may be inserted into the shaped part. A pin 26 is in cut-out 24 below elongated hole 25 to secure the disposable. The shaped part is fixed in position by a magneto coupling which is made of two magnets 27, 28 inserted into the shaped part and two magnets 29, 30 inserted into dish 15. The fixation may easily be released by a mimic (not shown), in which magnets 29, 30 are released from magnets 27, 28 using a foot pedal. However, instead of a magneto coupling, other locking and unlocking devices may also be provided which may be actuated manually or automatically.

In the center of upper contact surface 17, dish 15 has a further cut-out 31. Cut-out 31 is a slot which is dimensioned such that fixation device 20 may be introduced into the dish from above. A further fixation device 32 is provided for securing the upper end of the disposable and for closing the slot.

Figure 6:
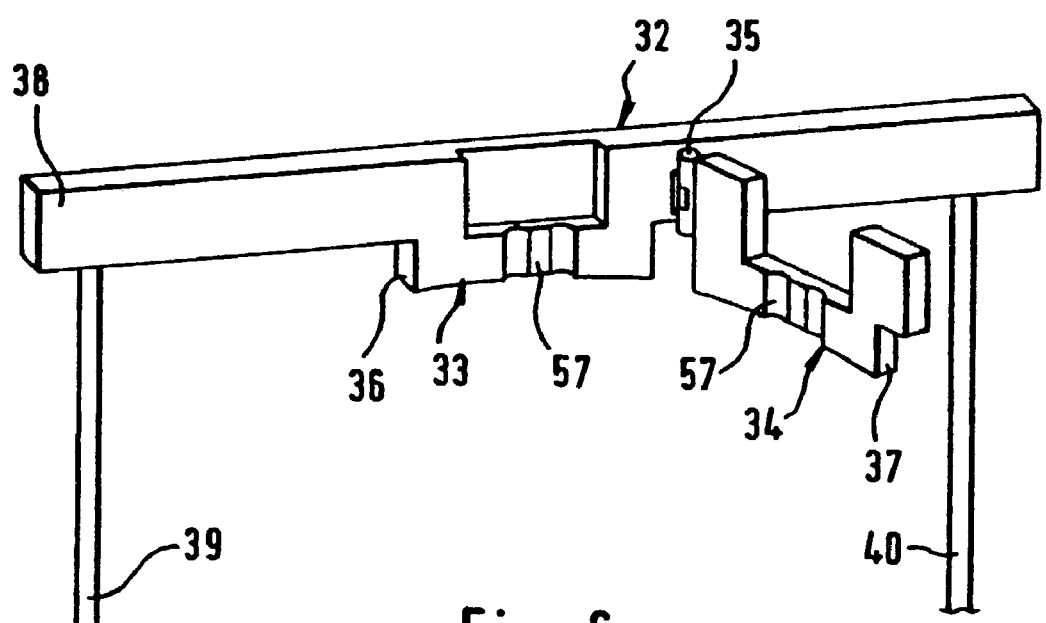
FIG. 6 shows the cut-away portion B of FIG. 4 in enlarged perspective representation.

FIG. 6 shows fixation device 32 in a perspective representation. Fixation device 32 has two shaped parts 33, 34, the one shaped part 34 being attached in a collapsible manner to the other shaped part 33 by a hinge fitting 35. Both shaped parts 33, 34 are provided with a lower section 36, 37 which are insertable with exact fit into slot 31 when the shaped parts are collapsed. Shaped part 36 is in one piece with a horizontal bar 38 to which vertical guide rods 39, 40 are attached which are guided so as to be movable in the longitudinal direction in lateral guide members 41, 42 of dish 15.

Lower sections 36, 37 of shaped parts 33, 34 have a contour which corresponds to the contour of upper contact surface 17. On the inner sides of both shaped parts 33, 34, a trough-shaped depression 57 is provided for accommodating connecting part 6 of the disposable.

Figure 4:
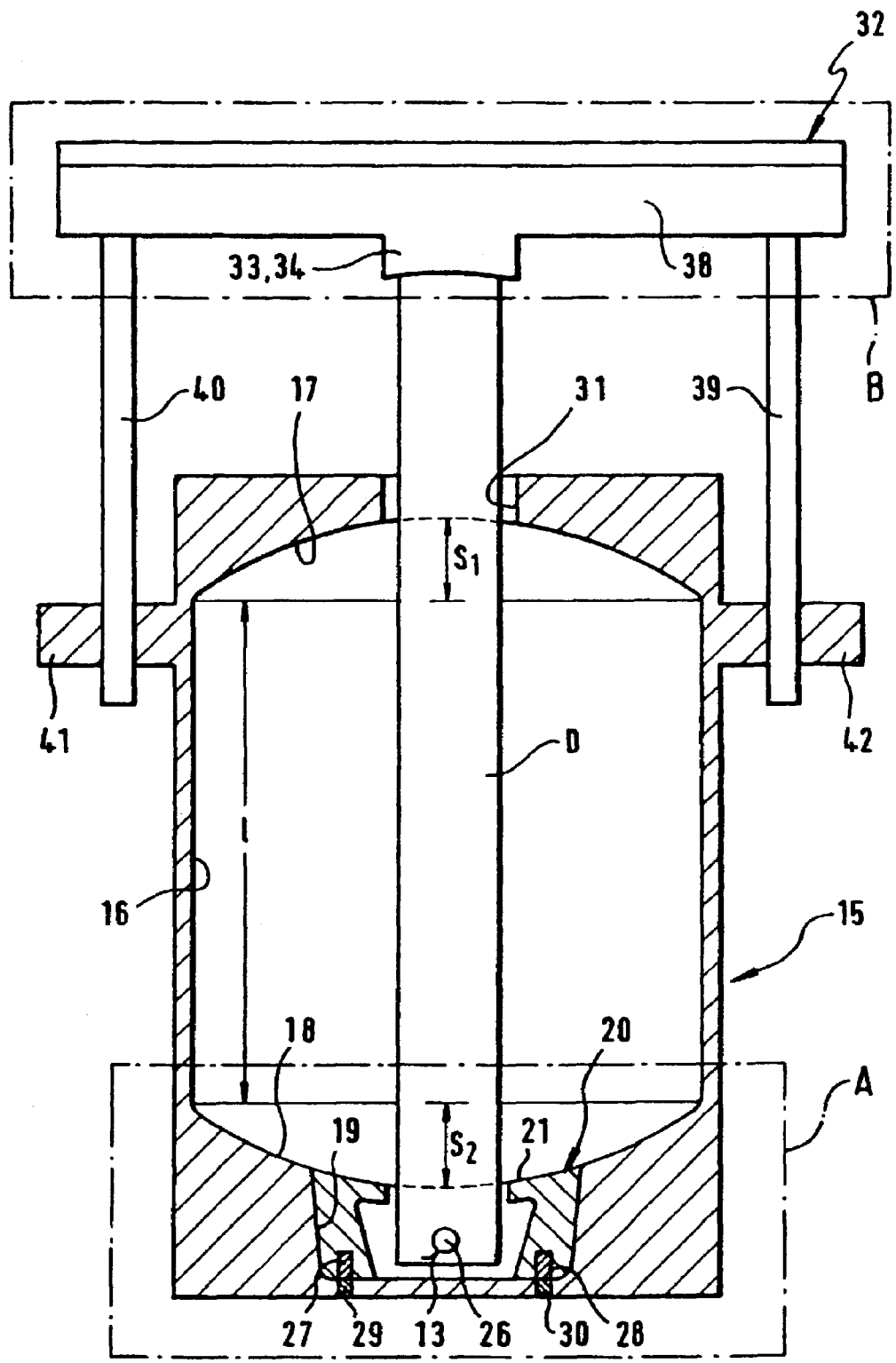
FIG. 4 shows a simplified representation of the receiving unit for the disposable from FIG. 1.

For the medical treatment, the lower end of folded disposable D is slipped through cut-out 25 of lower fixation device 20, and the disposable is suspended on pin 26 with the aid of rivet 13 forming a grommet. Lower fixation device 20 is then lowered with the disposable attached until the fixation device closes lower cut-out 19 of the dish. The lower end of the disposable is thereby fixed in position. Upper connecting part 6 of the disposable is thereupon inserted into trough-shaped depression 57 of upper fixation device 32 and is locked by collapsing shaped parts 33, 34. Thus, the upper end of the disposable is also fixed in position (FIG. 4).

During filling, the air between the film bag and dish 15 is forced out via a ventilation opening (not shown) in the dish.

Figure 7:
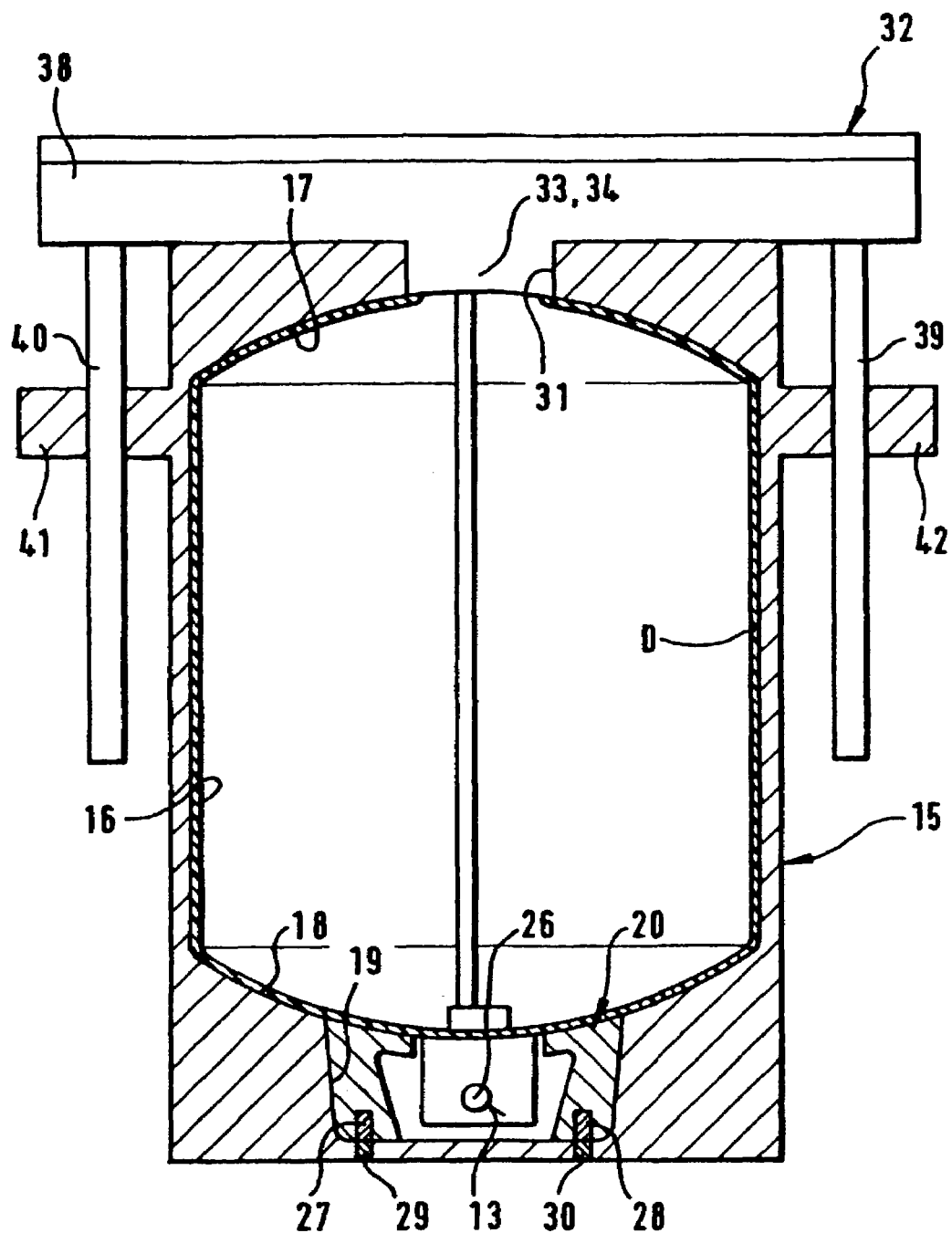
FIG. 7 shows the receiving unit of FIG. 4 into which the disposable of FIG. 1 is inserted.

During the filling of the disposable with fluid, the film bag unfolds in the dish. When the film bag unfolds in the dish, because of the shortening of the film bag, upper fixation device 32 shifts until it completely closes upper cut-out 31 (FIG. 7). The cylindrical section of the filled film bag now lies, without creases, against the cylindrical section of the dish. The outwardly curved upper and lower sections of the film bag also lie, substantially free of creases, against the upper and lower contact surfaces of the dish, so that an exactly reproducible form is given.

Figure 8:
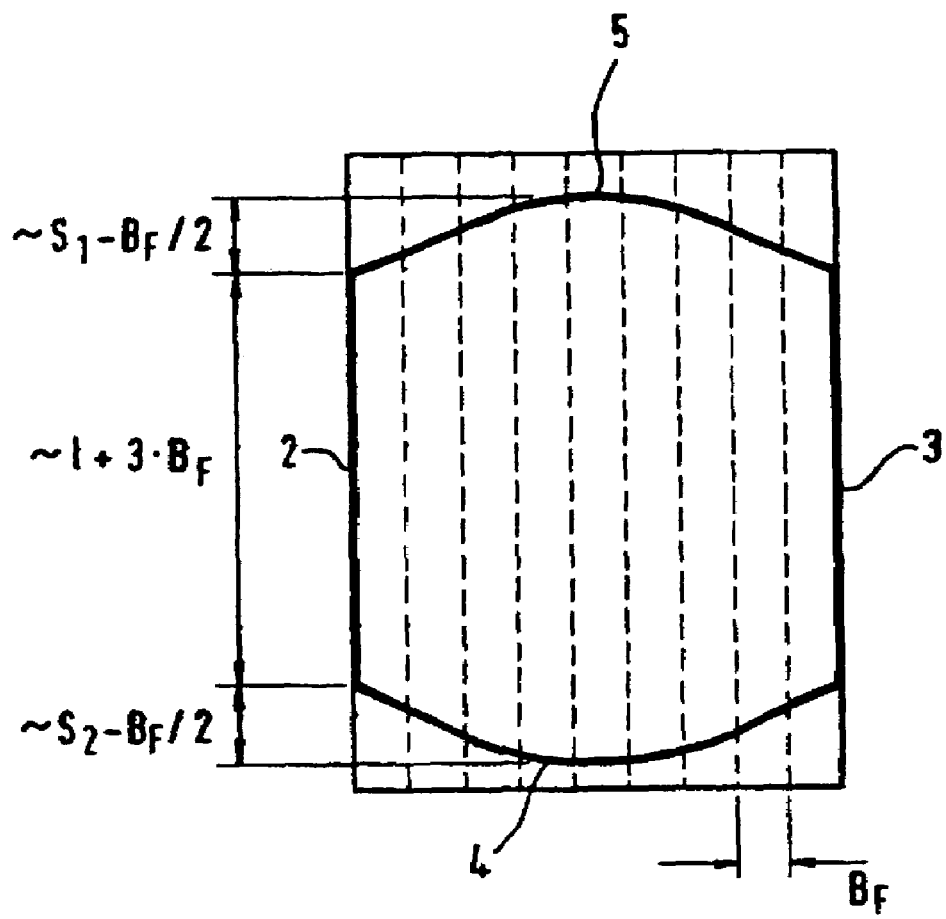
FIG. 8 shows the welded seams of the disposable from FIG. 1 which are adapted to the receiving unit.

FIG. 8 shows a disposable which can be unfolded particularly simply and has only a particularly slight tendency to form creases in its upper and lower sections. The reference numerals correspond to the reference numerals of the disposable described with reference to FIGS. 1 through 3. The length of both longitudinal welded seams 2, 3 of the flat-lying film bag is greater than length l of the cylindrical section of dish 15. It is greater by an amount that is roughly at least twice as large as width $B_F$ of the folds of the film bag. An optimal adaptation to the dish is achieved if the length of longitudinal welded seams 2, 3 is greater by an amount that is approximately three times as large as fold width $B_F$. The distance between the middle points of the straight lines running through the opposite ends of curved welded seams 4, 5 and the summits of the curved welded seams is less than the height or depth $S_1$, $S_2$ of outwardly curved sections 17, 18 of dish 15. It has proven to be optimal if the distance between the summits and the middle points of the straight lines is less by approximately half of fold width $B_F$. Thus, the curved form receives a relatively flat profile, so that its outgoing ends may also be replaced by straight welded seams.

In the following description of an exemplary embodiment of the present invention, with reference to FIG. 9, a hemodialysis device is described which has a receiving unit according to FIGS. 4 through 7 and in which a disposable according to FIGS. 1 through 3 and 8, respectively, is used. The reference numerals of FIG. 9 correspond to the reference numerals of FIGS. 1 through 8.

The blood of the patient is fed via an arterial blood line 43, into which a blood pump 44 is switched, to blood chamber 45 of a dialyzer 48 divided by a semipermeable membrane 46 into two chambers 45, 47, and is returned to the patient via a venous blood line 49. The dialyzing fluid flows counter thereto through dialyzing-fluid chamber 47 of dialyzer 48.

The dialyzing fluid is made available in the disposable according to FIGS. 1 through 3 which is inserted into receiving unit 50, described with the aid of FIGS. 4 through 7, of the hemodialysis device.

The inlet of dialyzing-fluid chamber 47 of dialyzer 48 is connected via a feed line 51 to connection 8 of connecting part 6 of disposable D, while the outlet of the dialyzing-fluid chamber is connected via a return line 52, into which a dialyzing-fluid pump 53 is switched, to connection 7 of connecting part 6 of the disposable. Branching off from return line 52 upstream of connecting part 6 is an overflow line 54 which discharges into a receptacle 55 for receiving ultra-filtered fluid. However, overflow line 54 may also be connected directly to the disposable. To that end, however, it is necessary that the disposable be provided with a connecting part having three connections. A controllable flow restrictor 56 is switched into overflow line 54 to be able to usefully limit the ultra-filtration rate.

The tube connections to the disposable may be conventional connecting pieces. It is crucial that, for putting the dialysis device into operation, the disposable be connectible quickly to the tube-line system, and be detachable again for exchanging the disposable. It is also possible to form the tube-line system in one piece with the disposable.

To put the hemodialysis device into operation, disposable D is inserted into receiving unit 50 and filled with a quantity of dialyzing fluid sufficient for a dialysis treatment. The hemodialysis device is subsequently started. The fresh dialyzing fluid then flows from the upper half of the disposable into dialyzing-fluid chamber 47, and the used dialyzing fluid is fed again to the lower half of the disposable so that a mixture of fresh and used dialyzing fluid is avoided. In this connection, advantage is taken of the fact that, because of the heat losses occurring in the outer circuit, the dialyzing fluid which is fed back is always somewhat cooler than the fresh dialyzing fluid. A heat-insulating construction of the receiving unit may also contribute to keeping the radial temperature gradient small, and thus convection currents are avoided. The optimal stratification of fresh and used dialyzing fluid is also supported by the nearly cylindrical shape of the unfolded disposable.

Figure 9:
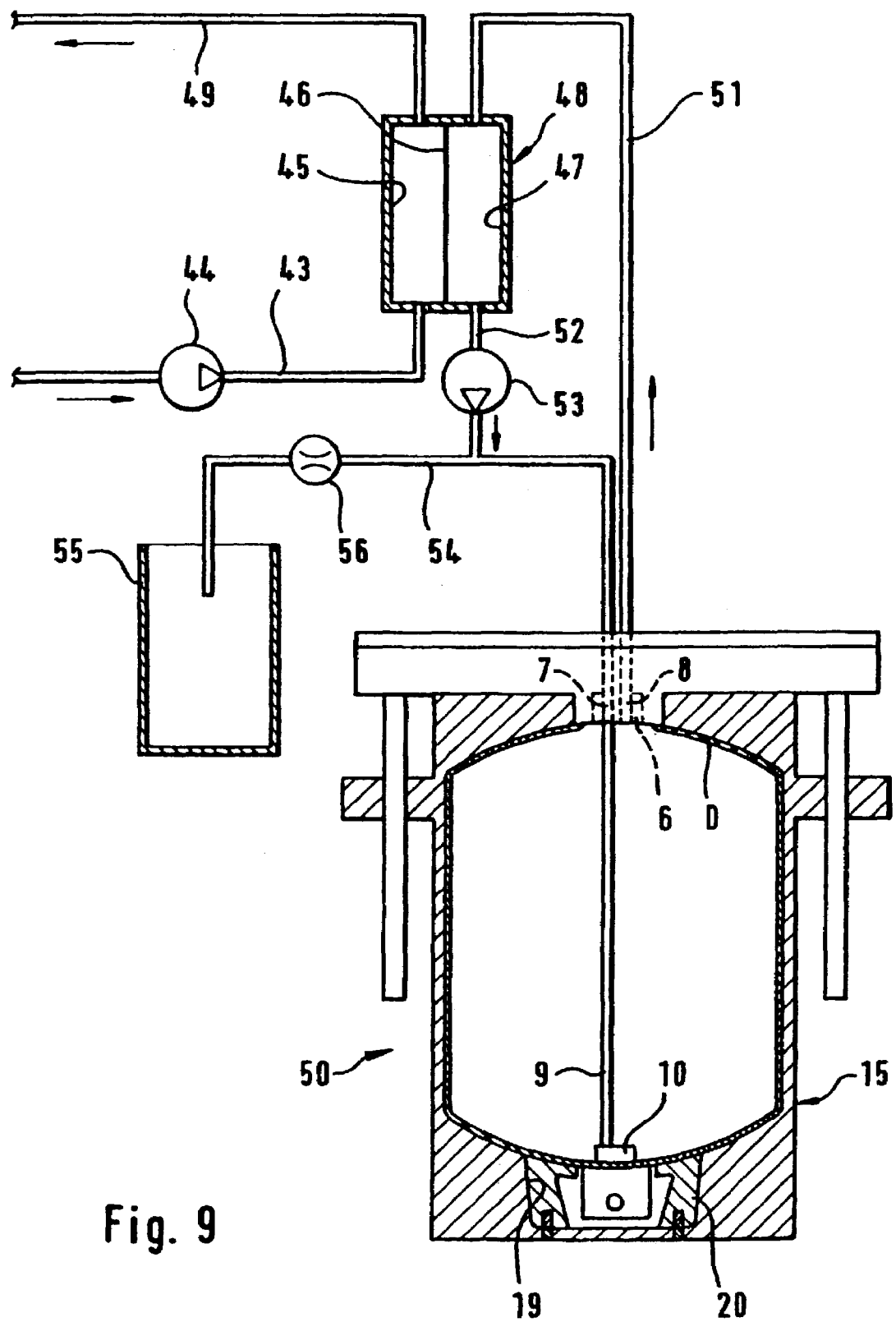
FIG. 9 shows a hemodialysis device having the receiving unit from FIG. 4 and the disposable from FIG. 1 in simplified representation.
Figure 10:
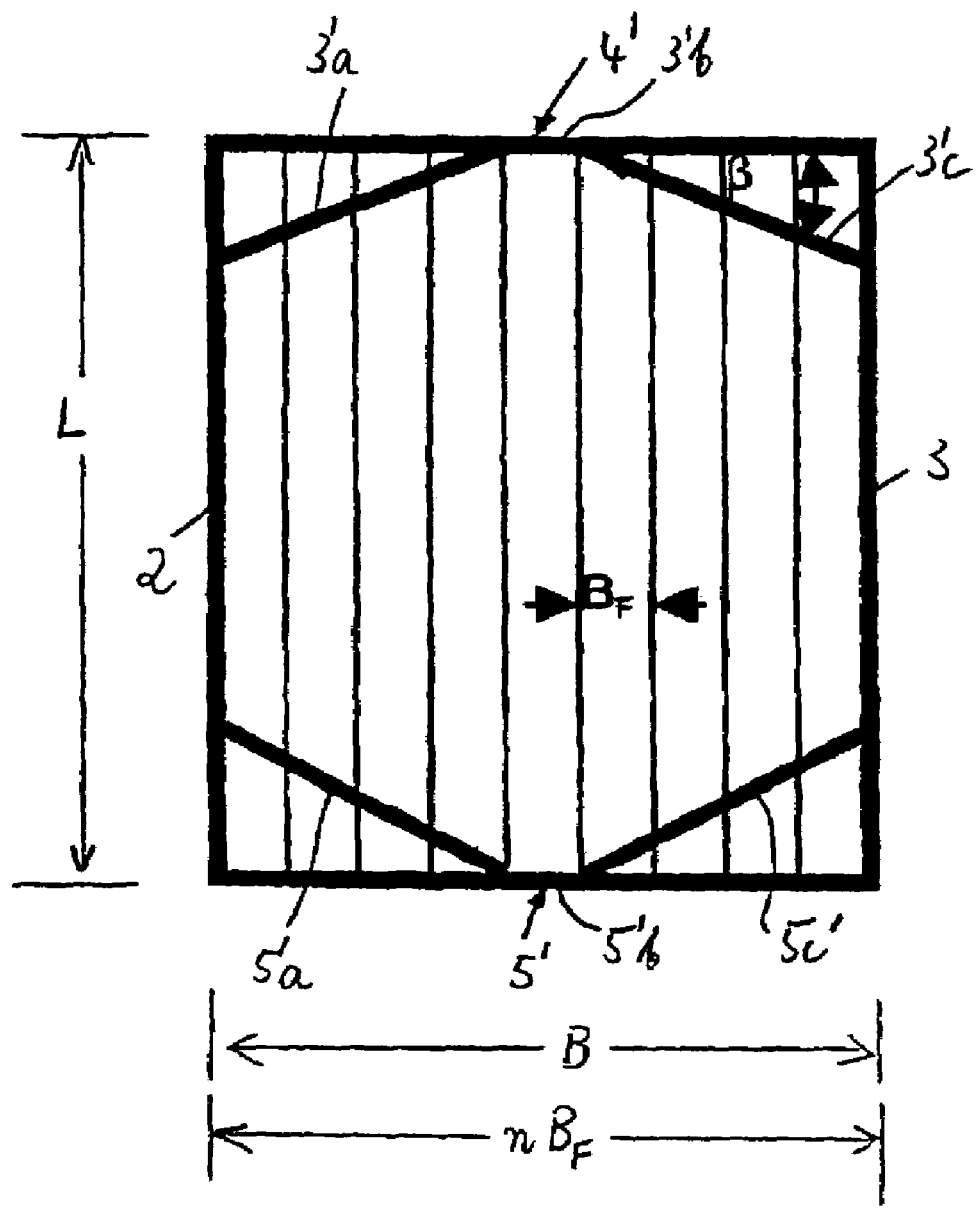
FIG. 10 shows a further exemplary embodiment of the disposable in the plan view.

FIG. 10 shows another exemplary embodiment of the disposable of the present invention in plan view, which is intended for the receiving unit of the hemodialysis device of FIG. 9. This specific embodiment differs from the exemplary embodiments described above due to the formation of the welded seams pointing outwardly. The mutually corresponding parts are provided with the same reference numerals.

The disposable has two rectangular films 1, 1' having the length L and the width B, which lie congruently one upon the other and are sealed at the longitudinal sides by longitudinal welded seams 2, 3 and at the ends by welded seams 4', 5' pointing outwardly. The flat-lying film bag is again folded repeatedly parallel to its longitudinal axis like a concertina in n sections of equal size, width $B_F$ of the fold sections being calculated from the quotient of width B of the flat films and the number of fold sections. The connecting part of the disposable is not shown in FIG. 10.

Each outwardly pointing welded seam is made of three straight sections 4'a, 4'b, 4'c and 5'a, 5'b, 5'c, respectively, which are easier to produce from the standpoint of production engineering than arched welded seams. Each of the two welded seams 4', 5' has a middle straight section 4'b, 5'b whose end points coincide with the outer edges of the middle fold. Outer straight sections 4'a, 4'c and 5'a, 5'c, respectively, join up at both sides of the middle straight section and extend at an angle β up to longitudinal welded seams 2, 3. Angle β is selected so that the outer straight sections optimally approximate the curved profile of the curved welded seams. It is calculated from the average rise of the arched weld.

What is claimed is:

1. A disposable for a device for carrying out a medical treatment using a fluid, the disposable comprising:
   a flat film bag comprising two superposed flat films, wherein the flat film bag is sealed by a first welded seam at its upper end in a position of normal use, and is sealed by a second welded seam at its lower end in the position of normal use;
   a connection for feeding the fluid to the disposable; and
   a connection for carrying the fluid away from the disposable;

wherein the flat film bag is repeatedly folded like a concertina parallel to its longitudinal axis which is vertical in the position of normal use.

2. The disposable as recited in claim 1, wherein the first welded seam and the second welded seam each have a profile deviating from a straight profile and pointing toward at least one of the upper end of the film bag and the lower end of the film bag in the position of normal use.

3. The disposable as recited in claim 2, wherein the first welded seam and the second welded seam are each arched.

4. The disposable as recited in claim 2, wherein the first welded seam and the second welded seam each comprise a plurality of straight sections.

5. The disposable as recited in claim 1, wherein the folded film bag includes folds which are fixed in position by at least one joining element.

6. The disposable as recited in claim 5, wherein the at least one joining element is disposed at the film end.

7. The disposable as recited in claim 1, further comprising:
   a connecting part welded to the film bag at the first welded seam, the connecting part comprising the connection for supplying fluid to the disposable and the connection for carrying fluid away from the disposable; and
   a tube line connected to the connection for supplying fluid to the disposable, wherein the tube line extends up to the second welded seam.

8. The disposable as recited in claim 7, further comprising:
   a fixation piece welded to the film bag at the second welded seam, wherein the tube line is secured to the fixation piece.

9. The disposable as recited in claim 1, wherein the two superposed flat films comprise a polyethylene base material including a polyamide sealing layer on one side.

10. A disposable for a device for carrying out a medical treatment using a fluid, the disposable comprising:
    a flat tubular film sealed by a first welded seam at its upper end in a position of normal use, and sealed by a second welded seam at its lower end in the position of normal use;
    a connection for feeding the fluid to the disposable; and
    a connection for carrying the fluid away from the disposable;
    wherein the flat tubular film is repeatedly folded like a concertina parallel to its longitudinal axis which is vertical in the position of normal use.

11. The disposable as recited in claim 10, wherein the first welded seam and the second welded seam each have a profile deviating from a straight profile and pointing toward at least one of the upper end of the tubular film and the lower end of the tubular film in the position of normal use.

12. The disposable as recited in claim 11, wherein the first welded seam and the second welded seam are each arched.

13. The disposable as recited in claim 11, wherein the first welded seam and the second welded seam each comprise a plurality of straight sections.

14. The disposable as recited in claim 10, wherein the folded tubular film includes folds which are fixed in position by at least one joining element.

15. The disposable as recited in claim 14, wherein the at least one joining element is disposed at the film end.

16. The disposable as recited in claim 10, further comprising:
    a connecting part welded to the tubular film at the first welded seam, the connecting part comprising the connection for supplying fluid to the disposable and the connection for carrying fluid away from the disposable; and
    a tube line connected to the connection for supplying fluid to the disposable, wherein the tube line extends up to the second welded seam.

17. The disposable as recited in claim 16, further comprising:
    a fixation piece welded to the tubular film at the second welded seam, wherein the tube line is secured to the fixation piece.

18. The disposable as recited in claim 10, wherein the tubular film comprises a polyethylene base material including a polyamide sealing layer on one side.

19. A method for producing a disposable for a device for carrying out a medical treatment using a fluid, the method comprising:
    superposing two flat films to form a flat film bag, wherein the flat film bag includes a connection for feeding the fluid to the disposable and a connection for carrying the fluid away from the disposable;
    sealing the flat film bag at its upper end in a position of normal use by a first welded seam;
    sealing the flat film bag at its lower end in the position of normal use by a second welded seam; and
    repeatedly folding the flat film bag like a concertina parallel to its longitudinal axis which is vertical in the position of normal use to form the disposable.

20. A method for producing a disposable for a device for carrying out a medical treatment using a fluid, the method comprising:
    sealing a flat tubular film at its upper end in a position of normal use by a first welded seam, wherein the flat tubular film includes a connection for feeding the fluid to the disposable and a connection for carrying the fluid away from the disposable;
    sealing the flat tubular film at its lower end in the position of normal use by a second welded seam; and
    repeatedly folding the flat tubular film like a concertina parallel to its longitudinal axis which is vertical in the position of normal use to form the disposable.

21. A device for carrying out a medical treatment using a fluid, the device comprising:
    a receiving unit comprising a shaping dish, wherein the shaping dish holds a disposable, the disposable comprising:
      a flat film bag comprising two superposed flat films, wherein the flat film bag is sealed by a first welded seam at its upper end in a position of normal use, and is sealed by a second welded seam at its lower end in the position of normal use;
      a connection for feeding the fluid to the disposable; and
      a connection for carrying the fluid away from the disposable;
      wherein the flat film bag is repeatedly folded like a concertina parallel to its longitudinal axis which is vertical in the position of normal use;
    and wherein the shaping dish includes a middle cylindrical contact surface which is adjoined by an outwardly curved upper contact surface and an outwardly curved lower contact surface, wherein the outwardly curved upper contact surface includes a first cut-out for inserting the disposable.

22. The device as recited in claim 21, wherein the first cut-out comprises a slot in the center of the outwardly curved upper contact surface.

23. The device as recited in claim 21, wherein the outwardly curved lower contact surface includes a second cut-out in the center of the outwardly curved lower contact surface, wherein the shaping dish further includes a first fixation device for detachably securing the lower end of the film bag, and wherein the first fixation device is insertable with an exact fit into the second cut-out.

24. The device as recited in claim 23, wherein the first fixation device is capable of being arrested in the shaping dish.

25. The device as recited in claim 23, wherein the shaping dish further includes a second fixation device for detachably securing the upper end of the film bag, the second fixation device being insertable with an exact fit into the first cut-out.

26. The device as recited in claim 25, wherein the second fixation device is secured to a retaining device such that the second fixation device can be displaced longitudinally.

27. The device as recited in claim 21, wherein the distance between the end of the first welded seam and the end of the second welded seam is greater than the length l of the middle cylindrical contact surface.

28. The device as recited in claim 27, wherein the folded film bag includes folds with a width $B_F$, and wherein the distance between the end of the first welded seam and the end of the second welded seam is at least two times greater than the width $B_F$.

29. The device as recited in claim 27, wherein the distance between the summits of the first and second welded seams and a middle point of straight lines running through the ends of the first and second welded seams, given a flat-lying film bag, is less than the depth of the outwardly curved upper contact surface and the depth of the outwardly curved lower contact surface.

30. The device as recited in claim 29, wherein the folded film bag includes folds with a width $B_F$, and wherein the distance between the summits of the first and second welded seams and a middle point of straight lines running through the ends of the first and second welded seams, given a flat-lying film bag, is less than the depth of the outwardly curved upper contact surface and the depth of the outwardly curved lower contact surface by an amount that is approximately half as large as the width $B_F$.

31. A device for carrying out a medical treatment using a fluid, the device comprising:
a receiving unit comprising a shaping dish, wherein the shaping dish holds a disposable, the disposable comprising:
a flat tubular film sealed by a first welded seam at its upper end in a position of normal use, and sealed by a second welded seam at its lower end in the position of normal use;
a connection for feeding the fluid to the disposable; and
a connection for carrying the fluid away from the disposable;
wherein the flat tubular film is repeatedly folded like a concertina parallel to its longitudinal axis which is vertical in the position of normal use;
and wherein the shaping dish includes a middle cylindrical contact surface which is adjoined by an outwardly curved upper contact surface and an outwardly curved lower contact surface, wherein the outwardly curved upper contact surface includes a first cut-out for inserting the disposable.

32. The device as recited in claim 31, wherein the first cut-out comprises a slot in the center of the outwardly curved upper contact surface.

33. The device as recited in claim 31, wherein the outwardly curved lower contact surface includes a second cut-out in the center of the outwardly curved lower contact surface, wherein the shaping dish further includes a first fixation device for detachably securing the lower end of the tubular film, and wherein the first fixation device is insertable with an exact fit into the second cut-out.

34. The device as recited in claim 33, wherein the first fixation device is capable of being arrested in the shaping dish.

35. The device as recited in claim 33, wherein the shaping dish further includes a second fixation device for detachably securing the upper end of the tubular film, the second fixation device being insertable with an exact fit into the first cut-out.

36. The device as recited in claim 35, wherein the second fixation device is secured to a retaining device such that the second fixation device can be displaced longitudinally.

37. The device as recited in claim 31, wherein the distance between the end of the first welded seam and the end of the second welded seam is greater than the length l of the middle cylindrical contact surface.

38. The device as recited in claim 37, wherein the folded tubular film includes folds with a width $B_F$, and wherein the distance between the end of the first welded seam and the end of the second welded seam is at least two times greater than the width $B_F$.

39. The device as recited in claim 37, wherein the distance between the summits of the first and second welded seams and a middle point of straight lines running through the ends of the first and second welded seams, given a flat-lying tubular film, is less than the depth of the outwardly curved upper contact surface and the depth of the outwardly curved lower contact surface.

40. The device as recited in claim 39, wherein the folded tubular film includes folds with a width $B_F$, and wherein the distance between the summits of the first and second welded seams and a middle point of straight lines running through the ends of the first and second welded seams, given a flat-lying tubular film, is less than the depth of the outwardly curved upper contact surface and the depth of the outwardly curved lower contact surface by an amount that is approximately half as large as the width $B_F$.

* * * * *